(12) United States Patent
Ueda et al.

(10) Patent No.: US 12,315,150 B2
(45) Date of Patent: May 27, 2025

(54) PROGRAM FOR INDICATING HUNNER LESION, LEARNED MODEL, AND METHOD FOR GENERATING SAME

(71) Applicant: TOMO CO., LTD., Kyoto (JP)

(72) Inventors: Tomohiro Ueda, Kyoto (JP); Andrey Grushnikov, Tokyo (JP)

(73) Assignee: TOMO CO., LTD. (JP)

( * ) Notice: Subject to any disclaimer, the term of this patent is extended or adjusted under 35 U.S.C. 154(b) by 374 days.

(21) Appl. No.: 17/818,853

(22) Filed: Aug. 10, 2022

(65) Prior Publication Data

US 2022/0392063 A1   Dec. 8, 2022

Related U.S. Application Data

(63) Continuation of application No. PCT/JP2021/043293, filed on Nov. 25, 2021.

(30) Foreign Application Priority Data

Nov. 25, 2020   (JP) ................................. 2020-195447

(51) Int. Cl.
   *G06T 7/00*   (2017.01)
   *G06T 7/70*   (2017.01)

(52) U.S. Cl.
   CPC .............. *G06T 7/0012* (2013.01); *G06T 7/70* (2017.01); *G06T 2207/10068* (2013.01);
   (Continued)

(58) Field of Classification Search
   CPC ........ A61B 1/000094; A61B 1/000096; A61B 1/0638; A61B 1/307; G06N 20/00;
   (Continued)

(56) References Cited

U.S. PATENT DOCUMENTS 8,080,185 B2   12/2011   Luly et al.
10,166,068 B2 *   1/2019   Sachs ..................... A61B 18/24
(Continued)

FOREIGN PATENT DOCUMENTS

JP   2009066090 A   4/2009
JP   2017534322 A   11/2017
(Continued)

OTHER PUBLICATIONS

Kwang Jin Ko et al.,"Therapeutic effects of endoscopic ablation in patients with Hunner type interstitial cystitis," 12 the Dec. 2017, BJU International,2018,pp. 679-664.*

(Continued)

*Primary Examiner* — Omar S Ismail
(74) *Attorney, Agent, or Firm* — Price Heneveld LLP

(57) ABSTRACT

The present disclosure relates to a method for generating a learning model, a learned model, a program, and a controller of a bladder endoscope in which the program or the model is recorded. The method including: acquiring, as teaching data, endoscope image data on a Hunner lesion in a bladder; and generating the learning model by using the teaching data such that a bladder endoscope image serves as an input and the position indication of a Hunner lesion in the bladder endoscope image serves as an output. The program causing a computer to perform acquiring endoscope image data on a Hunner lesion in a bladder, inputting a target bladder endoscope image to a learning model in which a bladder endoscope image serves as an input and position-indication data on a Hunner lesion in an endoscope image serves as an output, and outputting the position indication of the Hunner lesion.

15 Claims, 7 Drawing Sheets

(52) U.S. Cl.
CPC .............. *G06T 2207/20081* (2013.01); *G06T 2207/20084* (2013.01); *G06T 2207/30096* (2013.01)

(58) Field of Classification Search
CPC ............ G06N 3/08; G06T 2207/10068; G06T 2207/20081; G06T 2207/20084; G06T 2207/30096; G06T 7/0012; G06T 7/0014; G06T 7/70; G16H 50/20
See application file for complete search history.

(56) References Cited

U.S. PATENT DOCUMENTS

| | | | |
|---|---|---|---|
| 2009/0069696 A1* | 3/2009 | Ueda ................. | A61B 1/0638 600/109 |
| 2009/0175819 A1* | 7/2009 | Priest ................ | C07K 14/555 435/7.1 |
| 2013/0102532 A1* | 4/2013 | Uger .................. | A61P 13/02 514/9.6 |
| 2017/0251159 A1* | 8/2017 | Ho Duc ............. | G06T 7/11 |
| 2020/0113975 A1* | 4/2020 | Meenan ............. | A61K 38/26 |

FOREIGN PATENT DOCUMENTS

| WO | WO-2018206357 A1 * | 11/2018 | .......... A61K 31/728 |
|---|---|---|---|
| WO | WO-2018206358 A1 * | 11/2018 | .......... A61K 31/728 |

OTHER PUBLICATIONS

Yukio Homma et al.,"Clinical guidelines for interstitial cystitis and hypersensitive bladder," May 24, 2016, International Journal of Urology (2016) 23,pp. 542-545.*

Muhannad Alsyouf et al.,"Direct Endoscopic Visualization Combined with Ultrasound Guided Access during Percutaneous Nephrolithotomy: A Feasibility Study and Comparison to a Conventional Cohort," Feb. 22, 2016, The Journal of Urology, vol. 196, Issue 1, Jul. 2016, pp. 227-230.*

John E. Tomaszewski et al., "Biopsy Features Are Associated With Primary Symptoms in Interstitial Cystitis: Results From the Interstitial Cystitis Database Study," May 22, 2001,Urology, vol. 57, Issue 6, Supplement 1, Jun. 2001,pp. 67-72.*

Kristene E Whitmore et al., "Hunner lesion versus non-Hunner lesion interstitial cystitis/bladder pain syndrome," May 30, 2019,International Journal of Urology (2019) 26 (Suppl. 1), pp. 26-31.*

Aram Kim et al.,"Improved efficacy and in vivo cellular properties of human embryonic stem cell derivative in a preclinical model of bladder pain syndrome," Aug. 21, 2017,Scientific Reports vol. 7, Article No. 8872 (2017), pp. 1-10.*

Teruyuki Ogawa et al.,"Recent Developments in Imaging in BPS/IC," Dec. 14, 2019,Current Bladder Dysfunction Reports (2019) 14,pp. 301-305.*

Whitmore, Kristene E., et al., "Hunner lesion versus non-Hunner lesion interstitial cystitis/bladder pain syndrome," International Journal of Urology, Mar. 18, 2019, pp. 26-34, vol. 26, Issue S1.

* cited by examiner

PROGRAM FOR INDICATING HUNNER LESION, LEARNED MODEL, AND METHOD FOR GENERATING SAME

CROSS-REFERENCE TO RELATED APPLICATIONS

The present application is a continuation application of International Patent Application No. PCT/JP2021/043293 filed on Nov. 25, 2021, which claims priority to Japanese Patent Application No. JP2020-195447, filed on Nov. 25, 2020, the entire disclosures of which are incorporated herein by reference.

TECHNICAL FIELD

The present invention relates to a program useful for indicating a Hunner lesion. More specifically, the present invention relates to a program for indicating a target Hunner lesion, a learned model, and a method for generating the same in the field of bladder abnormalities, in particular, interstitial cystitis.

BACKGROUND

Interstitial cystitis is a chronic disease that causes symptoms such as frequent urination, urinary urgency, and cystalgia or discomfort with bladder fullness. A seriously ill patient may urinate 60 times a day, which causes considerable influence and results in difficulty in daily life. Women are more likely to develop interstitial cystitis men. Among about 1.3 million patients of interstitial cystitis in the U.S., at least one million patients are female. Although epidemiological surveys have been frequently conducted, the cause of the disease has not been discovered yet. Furthermore, the definitions, criteria, and expressions of "interstitial cystitis" vary among countries and regions. Thus, a description of "interstitial cystitis" in the present application also includes the concepts of cystalgia and overactive bladder pains.

The criteria of case collection study (Interstitial Cystitis Data Base; ICDB)18) in the U.S. reflect criteria routinely used for interstitial cystitis in the U.S. In the criteria, cystoscopic findings are not preconditions. Moreover, NIDDK (National Institute of Diabates and Digestive and Kidney Diseases) provides criteria that have been frequently cited. However, the criteria are used for strictly selecting cases during study. The criteria require cystoscopic findings and thus are more strictly defined. Some reports show that only less than half of patients diagnosed as interstitial cystitis by ICDB criteria meet the criteria of NIDDK.

As a characteristic of interstitial cystitis, the types of interstitial cystitis are broadly divided into a Hunner type having Hunner lesions and a non-Hunner type having no Hunner lesions. Hunner lesions are unique rubefacient mucous membranes having no normal capillary structures. Pathologically, epitheliums frequently fall off (erosion), and neovascularization and clustered inflammatory cells are found in submucosa. The Hunner type endoscopically and pathologically has definite abnormal findings. The Hunner type is a unique rubefacient mucous membrane having no normal capillary structures. As described above, any international criteria have not been established, and thus a Hunner lesion may be referred to as a Hunner's ulcer or may be simply referred to as an ulcer depending upon the region.

The Hunner type is more likely to cause serious conditions and thus requires correct diagnoses and treatments at an earlier stage. However, as described above, the presence or absence of a Hunner lesion is not defined as a requirement of the diagnosis of interstitial cystitis in some regions. Since the definition of global standards and criteria have not been established yet, only a few doctors can carry out diagnosis of interstitial cystitis and Hunner lesions with correct knowledge. Hence, even if U.S. Pat. No. 8,010,185 about the diagnosis of interstitial cystitis has been disclosed by Tomohiro Ueda, one of the inventors of the present invention, potential patients are missed, and inappropriate diagnoses and treatments including a wrong diagnosis have been performed.

SUMMARY OF THE INVENTION

Technical Problem

The cause of the difficulty of the problem is that cystoscope observations are frequently avoided in some regions where cystoscope findings are not always required for the diagnosis of interstitial cystitis. In this case, it may be difficult to confirm Hunner lesions with accuracy, so that potential patients may be missed as described above. Even if cystoscope observations are conducted, doctors with insufficient knowledge may miss potential patients. Moreover, cystoscope observations are mostly conducted on patients who have felt bladder abnormalities. Thus, just a few opportunities of observations on normal bladders are provided and only a few cystoscope images of normal bladders are accumulated. Furthermore, some doctors do not have knowledge about how to distinguish normal bladders from abnormal bladders free of Hunner lesions. Such circumstances cause a vicious cycle of difficulty in the definition of global standards and criteria.

However, regardless of the knowledge and skill of doctors, if a versatile technique capable of accurately and quickly identifying a Hunner lesion of a patient is provided and if a technique capable of properly recognizing a normal bladder is provided, remarkable progress is made in all of an accurate diagnosis of interstitial cystitis, the rescue of interstitial cystitis patients, and international consensus building.

Solution to Problem

In order to solve the problem, the present invention includes a method for generating a learning model, the method including: acquiring, as teaching data, endoscope image data on a Hunner lesion in a bladder; and generating the learning model by using the teaching data such that a bladder endoscope image serves as an input and the position indication of a Hunner lesion in the bladder endoscope image serves as an output.

Furthermore, the present invention includes a program that causes a computer to perform processing for acquiring endoscope image data on a Hunner lesion in a bladder, inputting a target bladder endoscope image to a learning model in which a bladder endoscope image serves as an input and position-indication data on a Hunner lesion in an endoscope image serves as an output, and outputting the position indication of the Hunner lesion.

Furthermore, the present invention includes a learned model that uses a bladder endoscope image acquired by using a bladder endoscope system, the learned model including an input layer that receives the bladder endoscope image, an output layer in which position indication data on a Hunner lesion in the endoscope image serves as an output, and an intermediate layer having a parameter learned by using teaching data in which endoscope image data on the Hunner lesion in a bladder serves as an input and position indication data on the Hunner lesion in the bladder image serves as an output, the learned model causing a computer to function to input a target bladder endoscope image to the input layer, perform an operation in the intermediate layer, and output the position indication data on the Hunner lesion in the image.

Moreover, the learning-model generating method, the program, the learned model preferably include, as teaching data, at least one of endoscope image data on air in a bladder, endoscope image data on a normal bladder, and endoscope image data on abnormal bladders free of Hunner lesions.

Furthermore, the image data preferably includes both of an image of narrow band imaging and an image of white light imaging.

Moreover, process of determination whether a bladder is normal or not and outputting is preferably enabled, and a program or a learned model is preferably installed in the controller of a bladder endoscope.

The program and the learned model of the present invention can be implemented by using known configurations, for example, a controller or a server including a CPU, a GPU, a ROM, a RAM, and a communication interface. Moreover, the program and the learned model can be configured as cloud systems. Furthermore, the present invention preferably includes means that causes display means such as a display to indicate and display the position of an estimated Hunner lesion by visually recognizable means such as framing or coloring. Moreover, the present invention may be used as a system to be used independently of an endoscope or may be used in the controller of a bladder endoscope system in real time during an observation in a bladder.

Furthermore, a deep learning model is used in the present invention. Typically, deep learning using a neural network is used, and a convolutional neural network is preferably used. When an image is inputted, a convolutional neural network acts as estimating means for estimating the position of a Hunner lesion. The estimating means is not limited thereto unless the effect of the present invention is disabled.

A deep learning model includes a large number of internal parameters. The internal parameters are adjusted to obtain, contrary to input data, an output result closest to teaching data. This adjustment is generally called "learning." In order to generate a high-performance model, the amount and quality of teaching data (a set of input data and teaching data) used for learning is important in addition to a model structure and a learning method.

Teaching data in the present invention is an endoscope image of a Hunner lesion in a bladder. A model capable of indicating the Hunner lesion is generated by indicating and learning the Hunner lesion. As a result of study, it was found that air (bubbles) in a bladder may be identified as a Hunner lesion or a Hunner lesion may be indicated in a normal bladder (it is assumed that a shadow of wrinkles or a height difference in a normal bladder may affect the indication). Thus, in order to prevent these factors from being identified as Hunner lesions, air (bubbles) was learned as air (bubbles). Since a mucosal condition of a normal bladder is different from a bladder condition of interstitial cystitis regardless of the presence or absence of a Hunner lesion, images of abnormal bladders free of Hunner lesions were learned in addition to images of normal bladders.

In the present invention, normal bladders are learned to effectively eliminate a determination rate of false positives about normal bladders. Moreover, images of abnormal bladders free of Hunner lesions are learned to effectively avoid the determination of false positives about abnormal bladders free of Hunner lesions. Furthermore, if a model is generated to output a normal bladder as a normal bladder, a configuration for determining and indicating, as an abnormal bladder, an abnormal bladder free of Hunner lesions can be achieved.

In order to obtain algorithms with high accuracy, it is necessary to learn a large number of Hunner lesion patterns. However, only a small number of bladder endoscope images of interstitial cystitis patients has been globally accumulated. Tomohiro Ueda, one of the inventors, has accumulated the largest number of bladder endoscope images of interstitial cystitis patients (and normal bladder images and images of abnormal bladders free of Hunner lesions) in the world. Thus, a wide variety of Hunner lesion images has been accumulated, allowing learning of images of sufficient types and quality for generating a model. Moreover, images of both of narrow band imaging (NBI) and white light imaging (WLI) are learned in the present invention, so that the model is usable for images of NBI and WLI. In narrow band imaging, narrowband light of two wavelengths of blue (wavelength from 390 nm to 445) and green (wavelength of 530 nm to 550 nm) is emitted, and a microscopic vessel image is outputted with an enhanced contrast. Blue light indicates the presence or absence of a neovascular on a mucous membrane while green light indicates the presence or absence of a vessel deep under a mucous membrane. White light imaging is an observation using illumination light of primary colors of blue, green, and red from the tip of an endoscope. In actual diagnoses by doctors, lesions are more likely to be visually confirmed in narrow band imaging. However, it is assumed that the utilization rate of white light imaging is higher than that of narrow band imaging in the world including developing countries. In white light imaging, a lesion and a background look red, causing difficulty in diagnosis. The present invention is also applicable to white light imaging and thus is so versatile as to be useful for finding patients of interstitial cystitis and building an international consensus.

DESCRIPTION OF EMBODIMENTS

Dataset

Based on moving images captured by a bladder endoscope, correct information is added (annotation) to the moving images in the following steps:

1. A candidate image is extracted every ten frames from all frames, and a Hunner-lesion candidate image is selected;
2. Correct information is added to the selected image; and 3. In frames around the image to which the correct information has been added, the correct information is added to similar images.

Data to which the correct information has been added was divided into NBI and WLI to produce a database of still images. In an extracted image, a black area outside an endoscope image was erased by trimming. This processing obtains a pixel size of about 1000×900 pixels. Moreover, an annotation at the position of a Hunner lesion was made by software called Label me.

The number of moving images

TABLE 1

| Dataset | The number of moving images |
|---|---|
| Year 2016 | 1940 |
| Year 2017 | 1952 |
| Year 2018 | 2005 |
| Year 2019 | 2259 |
| Year 2020 | 64 |

Still-Image Database Configuration

TABLE 2

| | NBI The number of still images | WLI The number of still images |
|---|---|---|
| Normal image | 672 | 726 |
| Hunner lesion | 2758 | 1591 |
| Bubbles | 573 | 17 |

*Normal images include images of normal bladders and abnormal bladders free of Hunner lesions but do not include images having Hunner lesions.

Bubbles include images of normal bladders and images having Hunner lesions.

Figure 1:
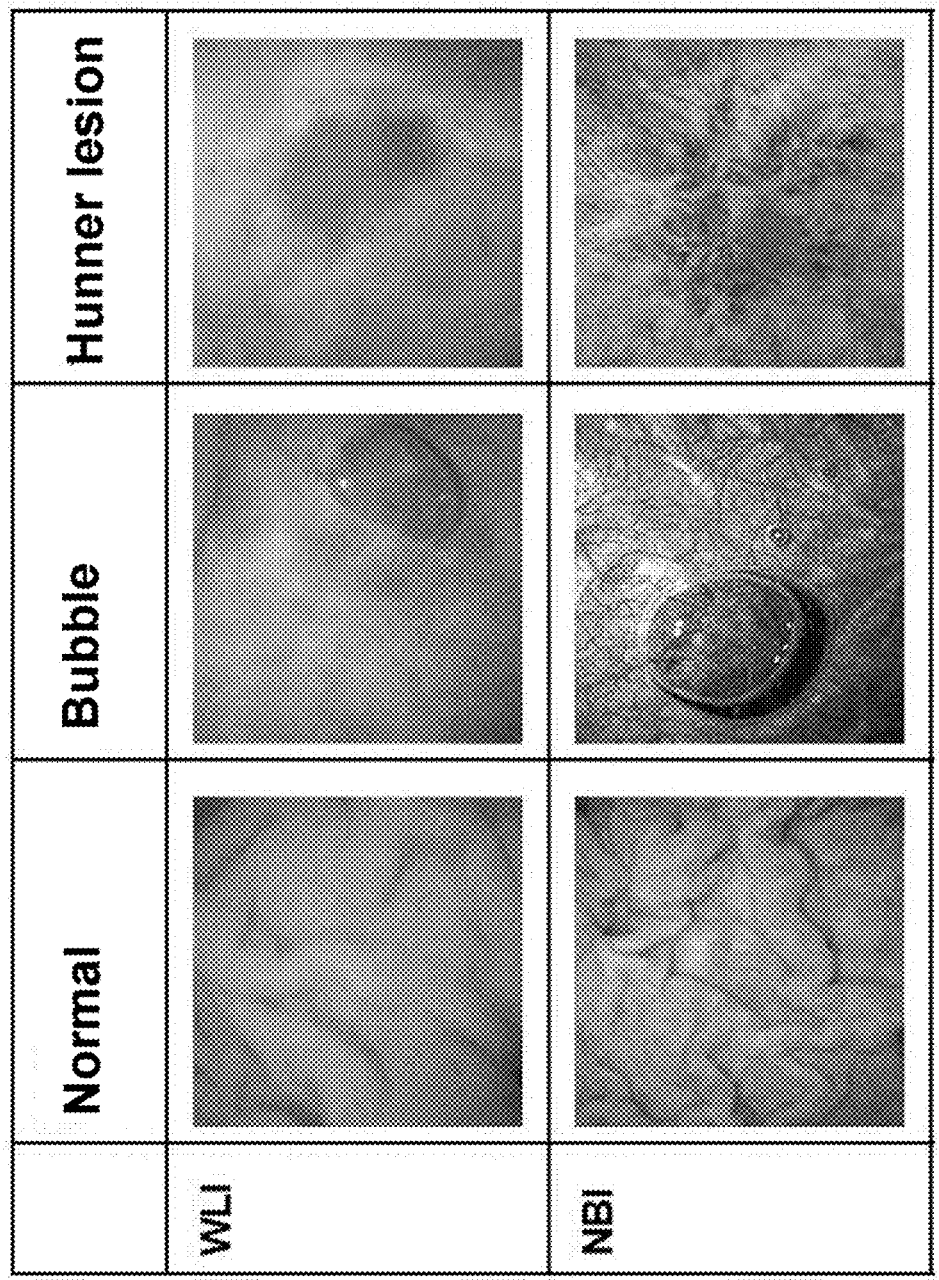
FIG. 1 shows examples of WLI and NBI images of a normal condition, bubbles, and a Hunner lesion.

FIG. 1 shows examples of WLI and NBI images of a normal condition, bubbles, and a Hunner lesion.

The image examples of bubbles in FIG. 1 are image examples of abnormal bladders free of Hunner lesions. Original images are all color images that clarify a difference in visibility between WLI and NBI, facilitating understanding of an advantage of NBI.

Model

An experiment was conducted by using a detection model and a segmentation model. The detection model is a model for estimating a rectangular area including a Hunner lesion area. The position and size of the rectangular area and the lesion confidence factor of the rectangle. The segmentation model is a model for outputting a lesion confidence factor for each pixel. A Hunner lesion area is estimated as well as the shape of the area.

In the experiment, models of high performance for a dataset of general images (COCO, CITYSCOPES) were used as follows:

Detection model: Cascade R-CNN;
Segmentation model: Cascade Mask R-CNN; and
Segmentation model: OCNet.

The three models were learned with data of NBI and WLI, and six models were created in total.

Experiment Setting and Result

In the experiment, the dataset was randomly divided into learning data of 85% and test data of 15% five times, and learning and evaluation were performed five times. The data was divided for each case. Tables 3 and 4 indicate the number of images and the number of cases in NBI and WLI datasets.

The number of images and the number of cases in NBI dataset

TABLE 3

| | Learning data | | Test data | |
|---|---|---|---|---|
| Divided dataset number | The number of images | The number of cases | The number of images | The number of cases |
| 1 | 3478 | 122 | 514 | 20 |
| 2 | 3478 | 122 | 514 | 20 |
| 3 | 3365 | 122 | 627 | 20 |
| 4 | 3361 | 122 | 631 | 20 |
| 5 | 3439 | 122 | 553 | 20 |

The number of images and the number of cases in WLI dataset

TABLE 4

| | Learning data | | Test data | |
|---|---|---|---|---|
| Divided dataset number | The number of images | The number of cases | The number of images | The number of cases |
| 1 | 1909 | 95 | 329 | 15 |
| 2 | 1969 | 95 | 269 | 15 |
| 3 | 1952 | 95 | 286 | 15 |
| 4 | 1773 | 95 | 465 | 15 |
| 5 | 1875 | 95 | 363 | 15 |

Three models (Cascade R-CNN, Cascade Mask R-CNN, OCNET) were learned for each image type and each divided dataset, and the performance of each model was evaluated based on the sensitivity and the positive prediction value of each Hunner lesion area. The sensitivity and the positive prediction value (PPV) are expressed as follows:

Sensitivity=#TP/(#TP+#FN) PPV=#TP/(#TP+#FP)
where #TP is the number of true positives, #FN is the number of false negatives, and #FP is the number of false negatives.

Figure 2:
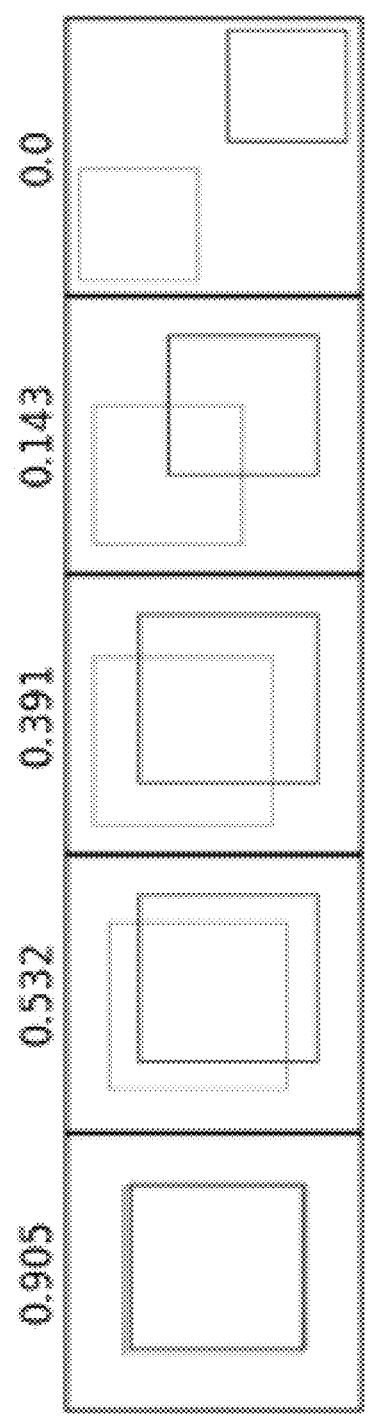
FIG. 2 shows a score example of an IoU.

A method for determining a true positive (TP), a false negative (FN), and a false positive for each Hunner lesion area will be described below. First, the degree of overlapping of a predicted area and a correct area is calculated by an IoU (Intersection over Union). The IoU is the ratio of the number of duplicate pixels in the predicted area and the correct area relative to the number of pixels in the union area of the predicted area and the correct area. If the two areas do not overlap each other at all, the IoU is 0, whereas if the two areas completely agree with each other, the IoU is 1. FIG. 2 shows a score example of the IoU for rectangular areas. Dotted lines indicate correct areas, and solid lines indicate predicted areas.

In the present example, TP, FN, and FP were defined as follows:

TP≡a correct area where the IoU exceeds 0.3 relative to all predicted areas, each including at least one duplicate pixel;

FN≡a correct area where the IoU is not larger than 0.3 relative to all predicted areas, each including at least one duplicate pixel; and FP≡a predicted area where the IoU is not larger than 0.1 relative to the correct area.

Figure 3:
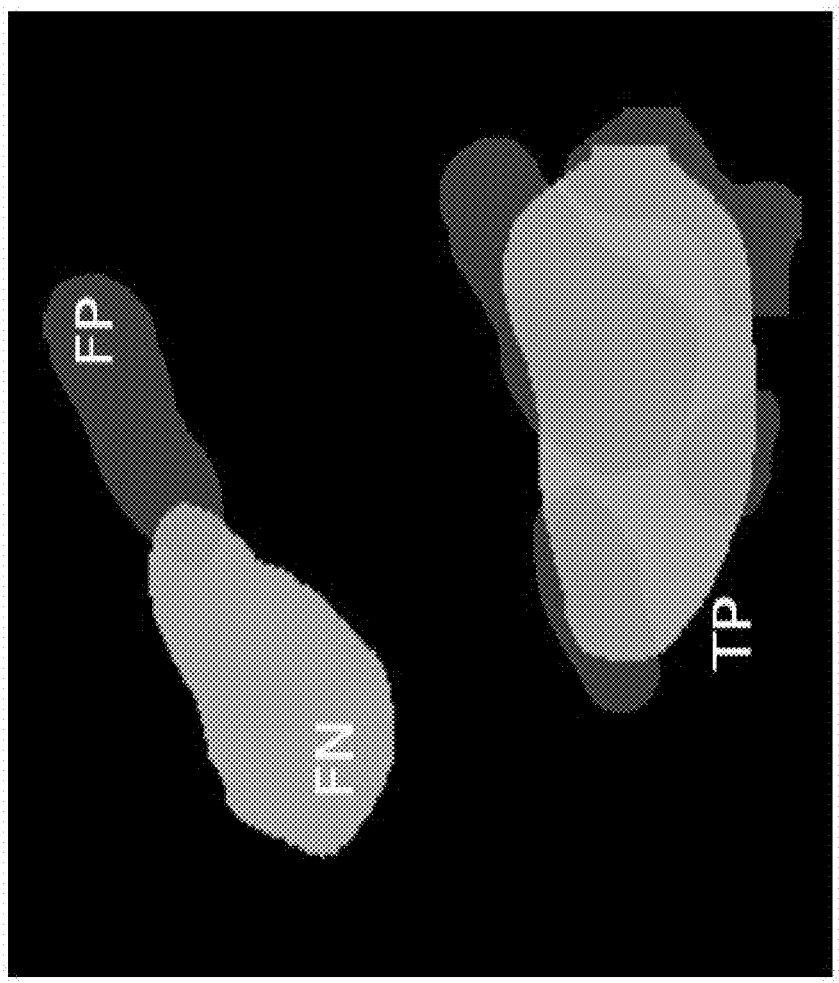
FIG. 3 is a conceptual diagram of TP, FP, and FN.

As described above, Cascade R-CNN, a detection model, is evaluated with rectangular regions. Cascade Mask R-CNN and OCNET, segmentation models, are evaluated in consideration of area shapes. The correct areas and the predicted areas are provided. As shown in FIG. 3, the upper correct area (left) and the upper predicted area hardly overlap each other and thus are denoted as FN and FP. The lower correct area (center) sufficiently overlapping multiple predicted areas is denoted as TP.

FIG. 3 shows a conceptual diagram of the TP, FP, and FN.

Tables 5 to 8 below show the evaluation results of each model. FIGS. 4 to 7 show the NBI image prediction results of each model. FIG. 6 shows a detection result example of NBI normal bladder images in the detection model and the segmentation model. The original images of FIGS. 4 to 7 are all color photos.

Table 5: the performance of the detection model (Cascade R-CNN) evaluated in an NBI image Table 6: the performance of the segmentation model evaluated in an NBI image Table 7: the performance of the detection model (Cascade R-CNN) evaluated in a WLI image Table 8: the performance of the segmentation model evaluated in a WLI image The performance of the detection model (Cascade R-CNN) evaluated in an NBI image

TABLE 5

| Divided dataset number | Evaluation in all predicted areas | | | | | Evaluation in predicted areas having a confidence factor of 50% or more | | | | |
|---|---|---|---|---|---|---|---|---|---|---|
| | TP | FP | FN | PPV | Sensitivity | TP | FP | FN | PPV | Sensitivity |
| 1 | 359 | 350 | 145 | 0.51 | 0.71 | 324 | 136 | 180 | 0.70 | 0.64 |
| 2 | 308 | 608 | 208 | 0.34 | 0.60 | 256 | 228 | 260 | 0.53 | 0.5 |
| 3 | 524 | 689 | 327 | 0.43 | 0.61 | 424 | 271 | 427 | 0.61 | 0.5 |
| 4 | 464 | 598 | 205 | 0.44 | 0.69 | 405 | 250 | 264 | 0.62 | 0.6 |
| 5 | 486 | 844 | 157 | 0.36 | 0.76 | 432 | 432 | 211 | 0.5 | 0.67 |
| Average | | | | 0.41 ± 0.068 | 0.67 ± 0.068 | | | | 0.59 ± 0.079 | 0.58 ± 0.078 |

The performance of the segmentation model evaluated in an NBI image

TABLE 6

| Divided dataset number | Cascade Mask R-CNN | | OCNET | |
|---|---|---|---|---|
| | PPV | Sensitivity | PPV | Sensitivity |
| 1 | 0.67 | 0.71 | 0.84 | 0.57 |
| 2 | 0.49 | 0.64 | 0.62 | 0.38 |
| 3 | 0.63 | 0.68 | 0.59 | 0.40 |
| 4 | 0.5 | 0.65 | 0.81 | 0.66 |
| 5 | 0.38 | 0.66 | 0.55 | 0.44 |
| Average | 0.53 ± 0.116 | 0.67 ± 0.027 | 0.68 ± 0.133 | 0.49 ± 0.120 |

*Evaluation with all prediction pixels (pixels with a confidence factor other than 0%) having reactions from the model The performance of the detection model (Cascade R-CNN) evaluated in a WLI image

TABLE 7

| Divided dataset number | Evaluation in all predicted areas | | | | | Evaluation in predicted areas having confidence fact of 50% or more | | | | |
|---|---|---|---|---|---|---|---|---|---|---|
| | TP | FP | FN | PPV | Sensitivity | TP | FP | FN | PPV | Sensitivity |
| 1 | 190 | 133 | 36 | 0.59 | 0.84 | 179 | 59 | 47 | 0.75 | 0.79 |
| 2 | 241 | 150 | 26 | 0.62 | 0.90 | 225 | 74 | 42 | 0.75 | 0.84 |
| 3 | 251 | 195 | 90 | 0.56 | 0.74 | 218 | 109 | 123 | 0.66 | 0.63 |

TABLE 7-continued

| Divided dataset number | Evaluation in all predicted areas | | | | | Evaluation in predicted areas having confidence fact of 50% or more | | | | |
|---|---|---|---|---|---|---|---|---|---|---|
| | TP | FP | FN | PPV | Sensitivity | TP | FP | FN | PPV | Sensitivity |
| 4 | 470 | 245 | 61 | 0.66 | 0.88 | 418 | 83 | 113 | 0.83 | 0.79 |
| 5 | 337 | 241 | 100 | 0.58 | 0.77 | 312 | 130 | 125 | 0.71 | 0.71 |
| Average | | | | 0.60 ± 0.039 | 0.83 ± 0.069 | | | | 0.74 ± 0.062 | 0.75 ± 0.083 |

The performance of the segmentation model evaluated in a WLI image

TABLE 8

| Divided dataset number | Cascade Mask R-CNN | | OCNET | |
|---|---|---|---|---|
| | PPV | Sensitivity | PPV | Sensitivity |
| 1 | 0.45 | 0.91 | 0.78 | 0.54 |
| 2 | 0.56 | 0.98 | 0.87 | 0.64 |
| 3 | 0.45 | 0.90 | 0.76 | 0.47 |
| 4 | 0.56 | 0.94 | 0.80 | 0.79 |
| 5 | 0.50 | 0.91 | 0.63 | 0.38 |
| Average | 0.50 ± 0.055 | 0.93 ± 0.032 | 0.76 ± 0.087 | 0.56 ± 0.158 |

Figure 4:
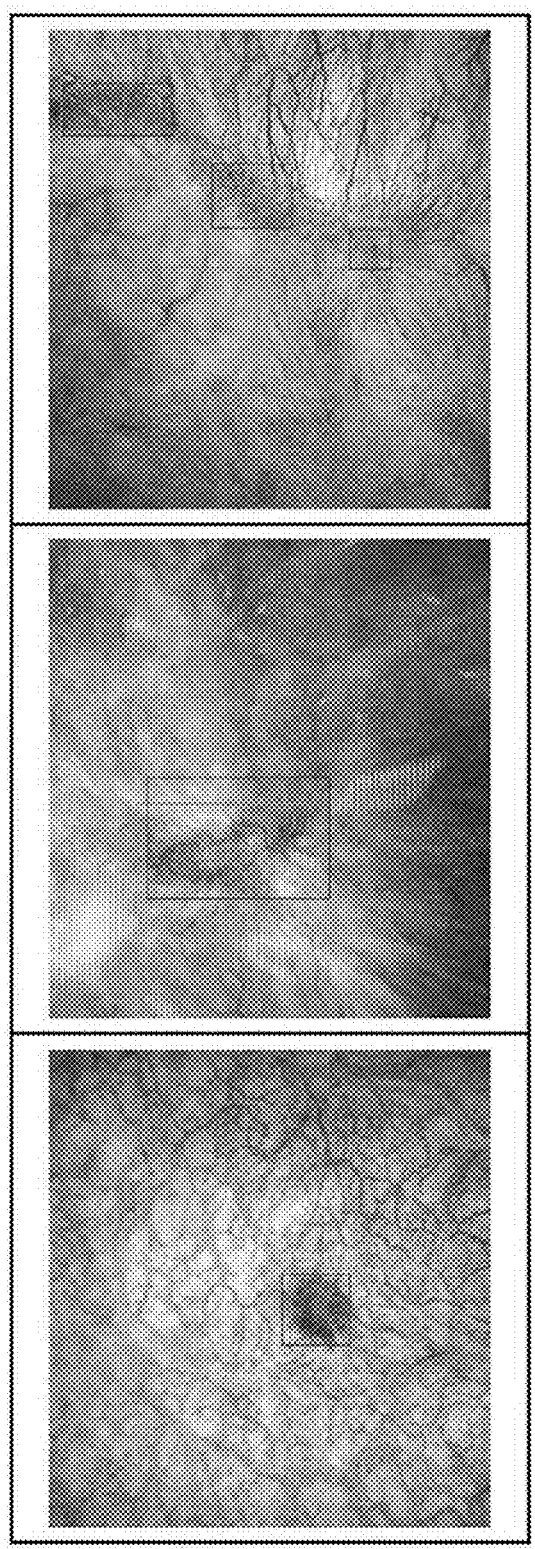
FIG. 4 shows an example of the NBI image prediction result of a detection model (Cascade R-CNN)

*Evaluation with all prediction pixels (pixels with a confidence factor other than 0%) having reactions from the model FIG. 4 shows an example of the NBI image prediction result of the detection model (Cascade R-CNN).

All predicted areas with a confidence factor other than 0% are displayed. Dotted lines (green in the original images) indicate correct areas, and solid lines (red in the original images) indicate predicted areas, which sufficiently indicates a Hunner lesion.

Figure 5:
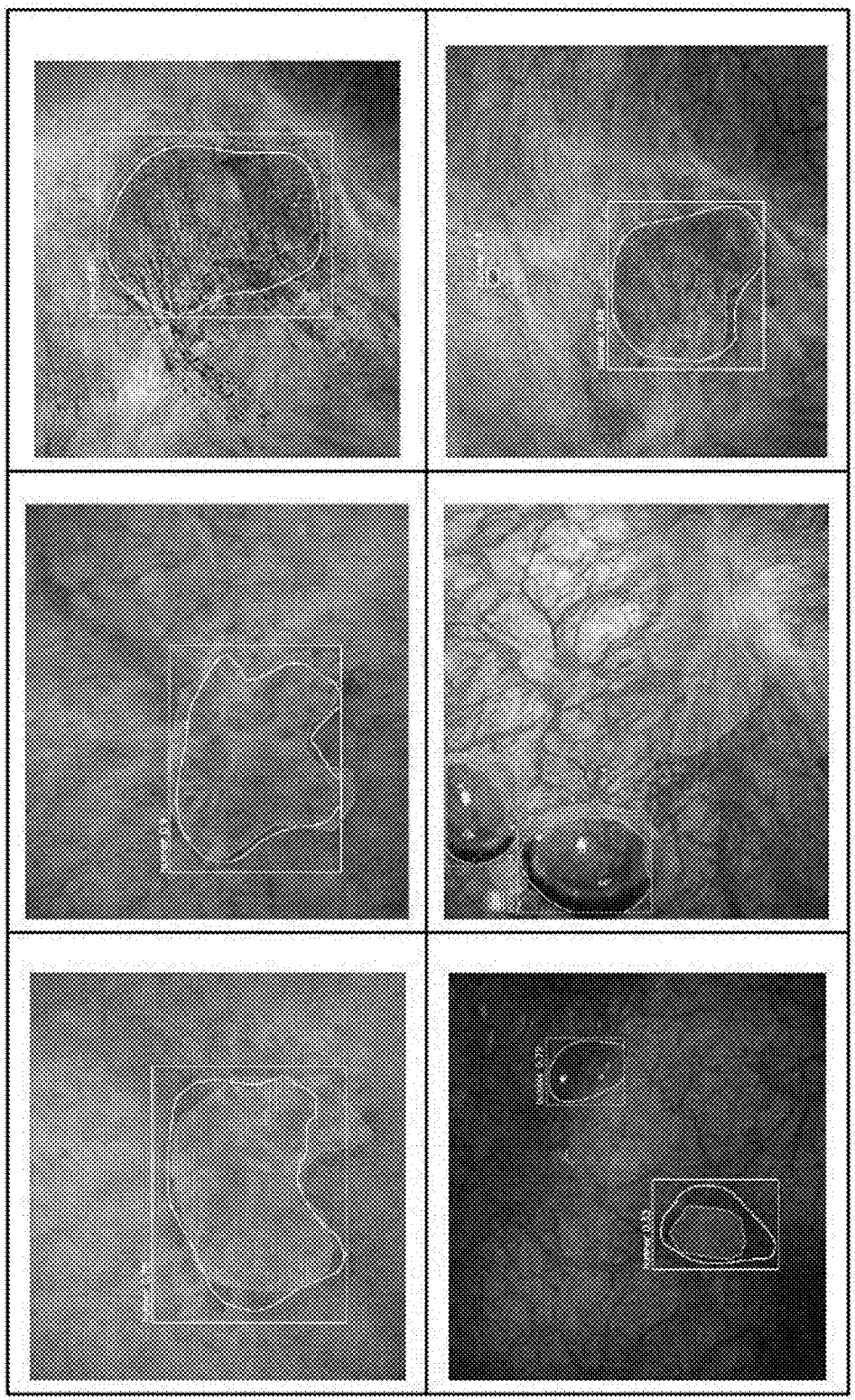
FIG. 5 shows an example of the NBI image prediction results of the detection model and a segmentation model.
Figure 6:
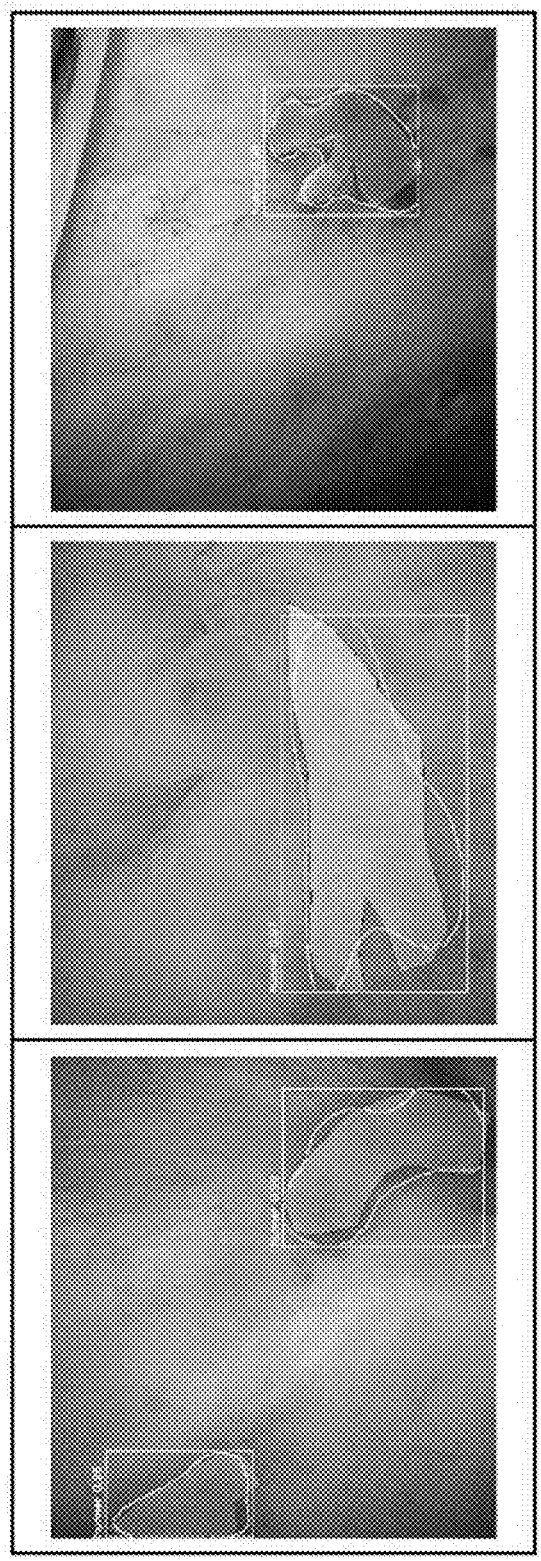
FIG. 6 shows an example of the WLI image prediction results of the detection model and the segmentation model.

FIG. 5 shows an example of the NBI image prediction results of the detection model and the segmentation model.

Rectangular outputs are displayed with confidence factors in addition to area specifications. An upper left image, an upper central image, and an upper right image sequentially indicate Hunner lesions with confidence factors of 0.78 (left), 0.9 (center), and 0.97 (right). A lower left image, a lower central image, and a lower right image sequentially indicate a Hunner lesion with a confidence factor of 0.33 and bubbles with a confidence factor of 0.79 (left), bubbles with a confidence factor of 0.97 (center), and a Hunner lesion with a confidence factor of 0.98 and a confidence factor of 0.4. In the present example, bubbles are indicated as bubbles in output display, so that the indication is successfully distinct from that of a Hunner lesion. In the original image, the correct area is indicated in green.

FIG. 6 shows an example of the WLI image prediction results of the detection model and the segmentation model.

Rectangular outputs are displayed with confidence factors in addition to area specifications. From the left to the right, a Hunner lesion is indicated with confidence factors of 0.96 and 0.99 (left), 0.97 (center), and 0.997 (right). This successfully provides a sufficient indication of a Hunner lesion. In the original image, the correct area is indicated in green.

Figure 7:
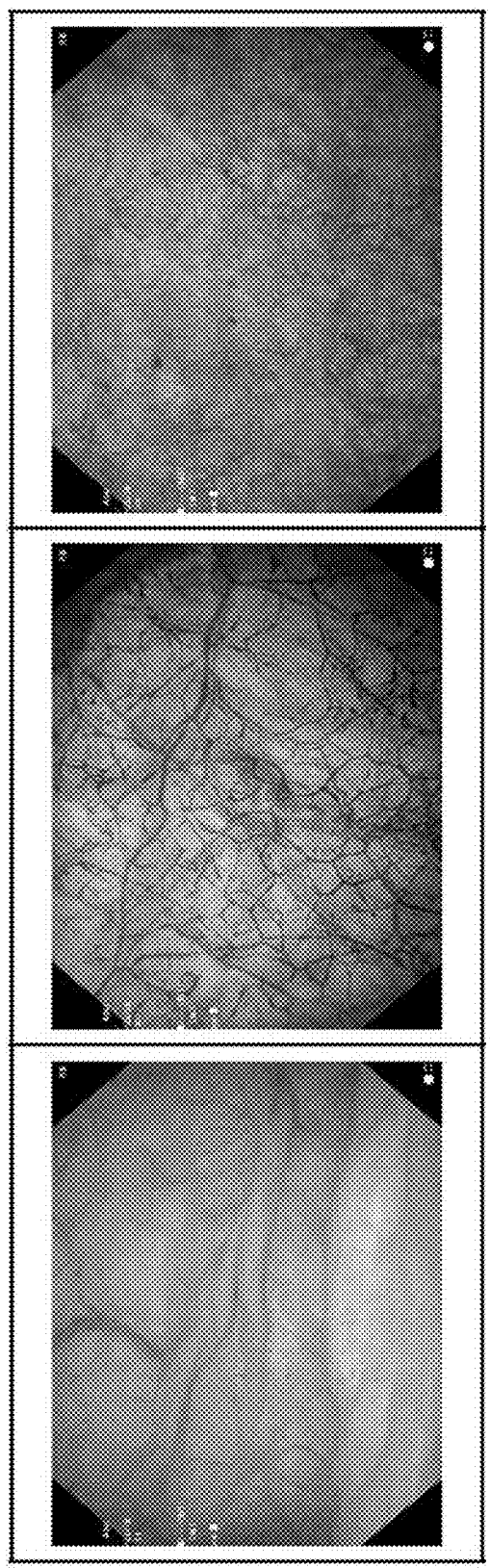
FIG. 7 shows a detection result example of NBI normal bladder images in the detection model and the segmentation model.

FIG. 7 shows a detection result example of NBI normal bladder images in the detection model and the segmentation model. In the normal bladder, any Hunner lesions have not been indicated. Determination of a false positive has been avoided even in a bladder having a different image appearance.

As described above, a learned model applicable to images of narrow band imaging and white light imaging can be formed. Moreover, bubbles can be indicated. According to the present invention, an opportunity can be provided to accurately and quickly identify a Hunner lesion in images of narrow band imaging and white light imaging regardless of the knowledge and skill of a doctor. Furthermore, determination of a false positive is avoided even if a height difference is made or a red phase is caused by a shadow or the like in a normal bladder. Consequently, the present invention contributes to the progress of an accurate diagnosis of interstitial cystitis, the rescue of interstitial cystitis patients, and international consensus building.

What is claimed is:

1. A method for generating a learning model, the method comprising:
    acquiring, as teaching data, endoscope image data on a Hunner lesion in a bladder, and
    generating the learning model by using the teaching data such that a bladder endoscope image serves as an input and position indication of a Hunner lesion in the bladder endoscope image serves as an output,
    wherein endoscope image data on a normal bladder and endoscope image data on an abnormal bladder free of Hunner lesions are further included as teaching data.

2. The method for generating a learning model according to claim 1, wherein endoscope image data on air in a bladder is further included as teaching data.

3. The method for generating a learning model according to claim 1, wherein the endoscope image data in the teaching data includes both of an image of narrow band imaging and an image of white light imaging.

4. The method for generating a learning model according to claim 3, wherein determination on whether a bladder in an inputted bladder endoscope is a normal bladder is further included as an output.

5. A program that causes a computer to perform processing for acquiring endoscope image data on a Hunner lesion in a bladder,
    inputting a target bladder endoscope image to a learning model in which a bladder endoscope image serves as an input and position-indication data on a Hunner lesion in an endoscope image serves as an output, and outputting position indication of the Hunner lesion,
    wherein the learning model further includes, as teaching data, endoscope image data on a normal bladder free of Hunner lesions and endoscope image data on an abnormal bladder free of Hunner lesions.

6. The program according to claim 5, wherein the endoscope image data in teaching data includes both of an image of narrow band imaging and an image of white light imaging.

7. The program according to claim 5, wherein endoscope image data on air in a bladder is further included as teaching data.

8. The program according to claim 6, further comprising processing for determining whether a bladder is normal or not and outputting the determination.

9. A controller of a bladder endoscope, wherein the program according to claim 5 is recorded.

10. A learned model that uses a bladder endoscope image acquired by using a bladder endoscope system, the learned model comprising:
    an input layer that receives an input of the bladder endoscope image;
    an output layer in which position indication data on a Hunner lesion in the endoscope image serves as an output, and
    an intermediate layer having a parameter learned by using teaching data in which endoscope image data on a Hunner lesion in a bladder serves as an input and position indication data on the Hunner lesion in the bladder image serves as an output,
    the learned model causing a computer to function to input a target bladder endoscope image to the input layer, perform an operation in the intermediate layer, and output the position indication data on the Hunner lesion in the image.

11. The learned model according to claim 10, wherein endoscope image data on air in a bladder is further included as teaching data.

12. The learned model according to claim 10, further comprising, as teaching data,
    endoscope image data on a normal bladder and
    endoscope image data on an abnormal bladder free of Hunner lesions.

13. The learned model according to claim 10, wherein the endoscope image data in the teaching data includes both of an image of narrow band imaging and an image of white light imaging.

14. The learned model according to claim 12, further comprising, as an output, whether a bladder is a normal bladder or an abnormal bladder.

15. A controller of a bladder endoscope, wherein the learned model according to claim 10 is recorded.

* * * * *